United States Patent
Carter

(10) Patent No.: US 8,311,640 B2
(45) Date of Patent: Nov. 13, 2012

(54) VARIABLE IMPEDANCE BYPASS PATHWAY FOR A TISSUE STIMULATING PROSTHESIS

(75) Inventor: Paul Carter, West Pennant Hills (AU)

(73) Assignee: Cochlear Limited, Macquarie University, NSW (AU)

( * ) Notice: Subject to any disclaimer, the term of this patent is extended or adjusted under 35 U.S.C. 154(b) by 70 days.

(21) Appl. No.: 13/062,436

(22) PCT Filed: Sep. 4, 2009

(86) PCT No.: PCT/AU2009/001155
§ 371 (c)(1),
(2), (4) Date: Mar. 4, 2011

(87) PCT Pub. No.: WO2010/025514
PCT Pub. Date: Mar. 11, 2010

(65) Prior Publication Data
US 2011/0166627 A1 Jul. 7, 2011

(30) Foreign Application Priority Data
Sep. 4, 2008 (AU) ................................. 2008904594

(51) Int. Cl.
*A61N 1/00* (2006.01)
(52) U.S. Cl. ........................................................ 607/62

(58) Field of Classification Search ..................... 607/62
See application file for complete search history.

(56) References Cited

U.S. PATENT DOCUMENTS

| | | |
|---|---|---|
| 3,752,939 A | 8/1973 | Bartz |
| 4,357,497 A | 11/1982 | Hochmair et al. |
| 5,123,422 A | 6/1992 | Charvin |
| 6,038,477 A | 3/2000 | Kayyali |
| 7,079,977 B2 * | 7/2006 | Osorio et al. ................. 702/176 |

OTHER PUBLICATIONS

International Search Report of PCT/AU2009/001155, dated Dec. 10, 2009, 5 pages.
Written Opinion of PCT/AU2009/001155, dated Dec. 10, 2009, 7 pages.

* cited by examiner

*Primary Examiner* — George Manuel
(74) *Attorney, Agent, or Firm* — Kilpatrick Townsend & Stockton LLP

(57) ABSTRACT

A method and apparatus for neural stimulation are disclosed. The principle is that a conventional current path is used to deliver the stimulus to neural structures, but an alternative current path is provided to bypass the neural structures during the opposite polarity part of the current flow. As a consequence, charge balance can be provided at the tissue/electrode interface, while delivering stimuli which are not charge balanced to the neural structures.

20 Claims, 11 Drawing Sheets

VARIABLE IMPEDANCE BYPASS PATHWAY FOR A TISSUE STIMULATING PROSTHESIS

CROSS-REFERENCE TO RELATED APPLICATIONS

This application is a national stage application of International Application No. PCT/AU2009/001155, filed Sep. 4, 2009, which claims priority to Australian Patent Application No. 2008904594, filed Sep. 4, 2008. The content of these applications are hereby incorporated by reference herein.

BACKGROUND

1. Field of Invention

The present invention relates generally to tissue stimulating prostheses, and in particular, to a controllable bypass pathway for a tissue stimulating prosthesis.

2. Related Art

Certain medical devices, sometimes referred to as tissue-stimulating prostheses, operate by delivering an electrical stimulation to a recipient. These prostheses include, but are not limited to, pain relief stimulators, cardiac pacemakers, neural or neuromuscular stimulators, hearing prostheses, visual prostheses, etc. Hearing prostheses, such as a cochlear implants, brain stem implants, etc, deliver neural stimulation to a recipient's auditory system so as to evoke perception of a sound.

Neural stimulation conventionally delivers charge balanced stimuli. That is, the stimulation includes balanced negative and positive charges, so that no net positive or negative direct current (DC) is delivered to the recipient's tissue. This use of charge balanced stimuli prevents or reduces the production of harmful by-products at that interface that would occur through delivery of a DC current across the electrode/tissue interface.

Typically, a biphasic pulse pair is used to achieve charge balance. Such a stimulus is delivered as a positive charge pulse in phase 1, and an equal negative charge pulse in phase 2. The negative charge pulse typically has the same current and period as the positive pulse, but may alternatively be applied over a longer period or at lower amplitude. The important feature is that the total charge in phases 1 (positive) and 2 (negative) are equivalent.

SUMMARY

In one aspect of the present invention, a tissue stimulating prosthesis implantable in a recipient to electrical stimulate a segment of the recipient's tissue with stimulating current signals having a first polarity during a first phase, and a second, opposite polarity during a second phase is provided. The prosthesis comprises: a stimulator unit configured to generate the current signals; a stimulating contact positioned adjacent the tissue; a reference electrode positioned separate from the stimulating contact; and a variable bypass pathway disposed between the stimulating contact and reference electrode, wherein the pathway has an impedance to current signals of the first polarity that is greater than the impedance of the tissue, and an impedance to current signals of the second polarity that is less than the impedance of the tissue.

In another aspect of the present invention method of electrically stimulating a segment of the recipient's tissue with a tissue stimulating prosthesis comprising a stimulator unit, a stimulating contact positioned adjacent the tissue, a reference electrode positioned separate from the stimulating contact, and a variable bypass pathway disposed between the stimulating contact and reference electrode is provided. The method comprises: conducting a first polarity of current signals from the stimulating contact to the reference electrode via the tissue; and conducting a second polarity of current signals from the stimulating contact to the reference electrode at least partially through the variable bypass pathway.

BRIEF DESCRIPTION OF THE DRAWINGS

Illustrative embodiments of the present invention will now be described with reference to the accompanying figures, in which.

DETAILED DESCRIPTION

Figure 1:
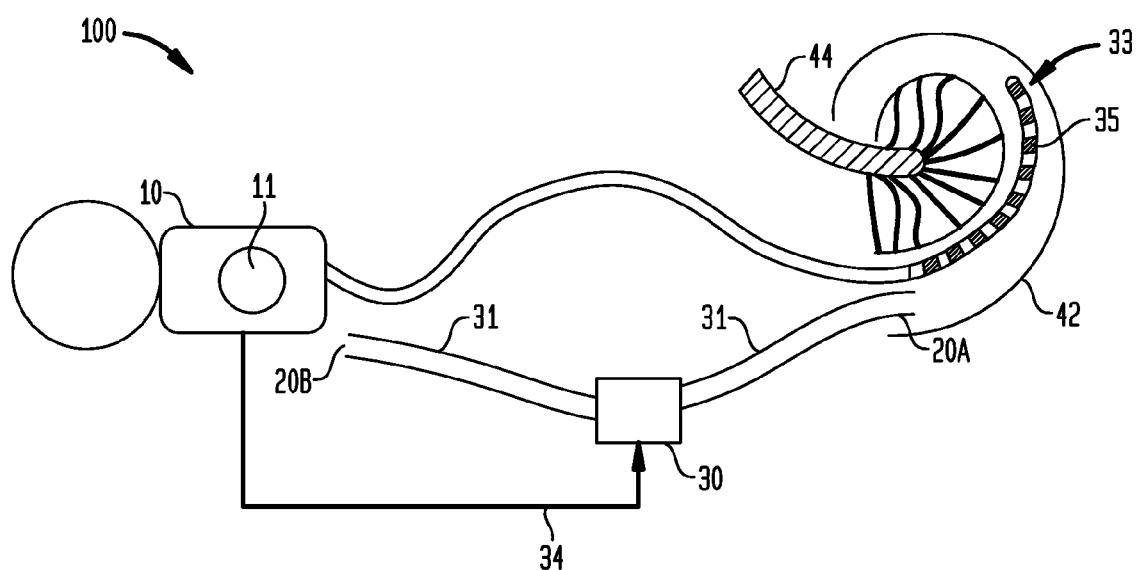
FIG. 1 is schematic diagram of a cochlear implant, in accordance with one embodiment of the present invention.

Embodiments of the present invention are generally directed to a tissue stimulating prosthesis implantable in a recipient to electrical stimulate a segment of the recipient's tissue with stimulating current signals having a first polarity during a first phase, and a second, opposite polarity during a second phase. The prosthesis includes a stimulator unit that generates the current signals, and a stimulating contact positioned adjacent the tissue to deliver the current signals. The prosthesis also includes a reference electrode positioned separate from the stimulating contact; and a variable bypass pathway disposed between the stimulating contact and reference electrode, wherein the pathway has an impedance to current signals of the first polarity that is greater than the impedance of the tissue, and an impedance to current signals of the second polarity that is less than the impedance of the tissue. In operation, the first polarity current is conducted from the stimulating electrode to the return electrode through the population of nerve cells, while the second pulse of current at least partially bypasses the population of nerve cells and is conducted through the variable impedance pathway.

More specifically, the variable impedance bypass pathway includes one or more impedance control element that has an impedance that may be changed, or has a different impedance to positive and negative current. The impedance control elements may be one or more ion switches, or may be one or more ion permeable membranes that only allow the flow of ions in one direction. In each instance, these impedance is referred to herein as being variable because the impedance changes, or is substantially different to different polarities.

The inventors of the present application have recognized that, if charge is delivered to the nerve using only one polarity, or at least with a net excess of one polarity, then less charge overall would be needed for the equivalent stimulation level. This would result in less overall power being used by the system. For example, different parts of the neural population "fire" (i.e. generate action potentials to rely electrical current) in response to different levels of electrical stimulation. In a biphasic stimulation scheme in which a current signal comprises a positive pulse (phase 1) followed by an equivalent negative pulse (phase 2), a segment of the nerve population is brought close to the firing threshold, but are not caused to fire. As such, this segment of nerves could be subsequently fired through application of relatively little additional positive current being. However, in conventional implants, to preserve charge balance, the negative current applied in phase 2 reverses the effect of phase 1 on the segment population of nerves, and returns them to closer to their unstimulated state (i.e. pre-phase 1). This means that much more charge must be used to fire that population of nerves, particularly in the next stimulation cycle, than would have been necessary without phase 2.

As such, as noted above, the bypass pathway in accordance with embodiments of the present invention reduces the flow of the negative current through a substantial amount of the nerve population so as to retain any stimulated nerve populations in the stimulated state. Accordingly, less current may then be used to cause the nerve populations to subsequently fire.

The present invention will be described with reference to a particular illustrative tissue stimulating prosthesis, namely a cochlear implant. It will be appreciated that these illustrative examples are not intended to be limitative of the scope of the present invention, and many variations and additions are possible. For example, embodiments of the present invention may be used in any device that utilized electrical neural stimulation, such as pain relief stimulators, cardiac pacemakers, neural or neuromuscular stimulators, visual prostheses, or other electrically stimulating hearing prosthesis, such as a hybrid electrical/acoustic systems, brain stem implants, etc. Additionally, embodiments of the present invention may be utilized in fully or partially implantable systems, or fully external systems.

As noted above, in electrical stimulation positive and negative charge pulses are delivered. For ease of description, the positive pulses will be considered to be the desired stimulation, and the negative pulses are used to ensure charge balance. It will be appreciated that, in practice, either polarity may be effective to evoke a desired response.

FIG. 1 is a schematic diagram a cochlear implant 100 in accordance with embodiments of the present invention. As shown, cochlear implant 100 includes an implantable receiver/stimulator unit 10, and an array of stimulating contacts, shown as electrode array 33 implanted in the scala tympani 42 of a recipient. An extracochlear electrode 11 is positioned outside the cochlea for use in a monopolar stimulation mode. In the monopolar stimulation mode, a potential difference causing a current pulse is between a selected intracochlear electrode 35 and extracochlear electrode 11.

In the embodiments of FIG. 1, cochlear implant 100 further includes a bypass pathway 18 comprising an impedance control element in the form of ion switch 30 and silicone tubing 31. Implant 100 further includes, a control cable 34 electrically connecting receiver/stimulator unit 10 to ion switch 30. The distal end 20A of silicone tube 31 is positioned inside the cochlea, and the proximal end 20B is adjacent to extracochlear electrode 11. As shown, ion switch 30 is positioned between one half tubing 31A and a second half 31B. Ion switch 30 is controlled by an external control signal. The control signal acts to vary the mobility of the ions flowing through the switch, which in turn changes the impedance between the two sides of the switch. Ideally the switch would have zero impedance in the "on" condition and infinite impedance in the "off condition.

For the purposes of a cochlear implant, the ion switch must be able to change its state in a few microseconds so that it can be synchronized to the two phases of a biphasic cochlear implant stimulation current signal, which are typically a few tens of microseconds in duration. It will be understood that the timing required is a function of the type of neural stimulations being used, so that for systems using slower pulse regimes the ion switch may be able to be correspondingly much slower.

Figure 2:
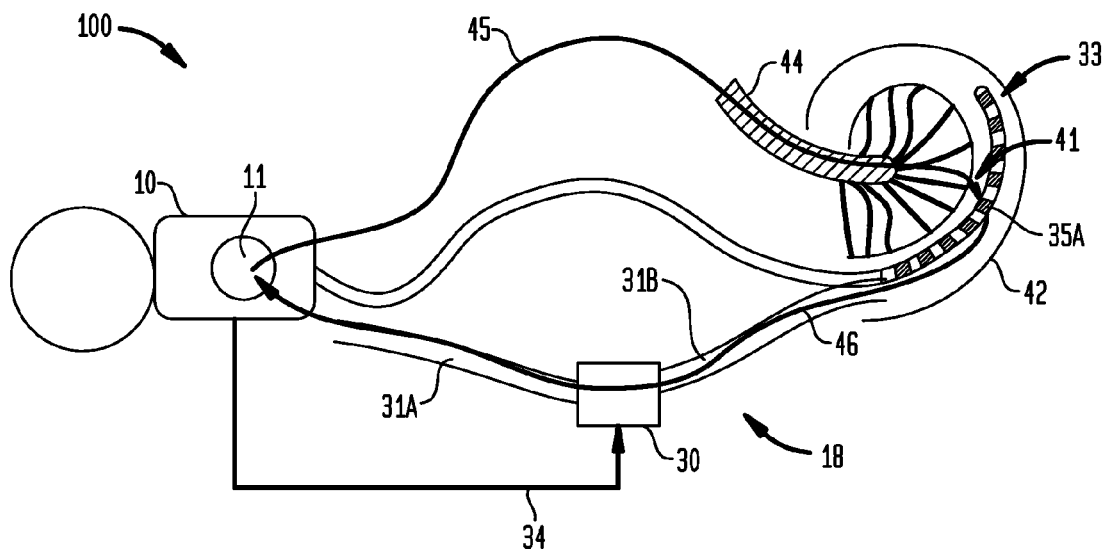
FIG. 2 illustrated the cochlear implant of FIG. 1 and arrows schematically showing the flow of current in different phases.

As noted above, for ease of description, embodiments of the present invention are described herein with reference to current having two phases, a first phase (phase 1) comprising a positive pulse, and a second phase (phase 2) comprising a negative pulse. FIG. 2 is another schematic diagram of cochlear implant 100, but further schematically illustrates the difference in current flow during these two phases. More specifically, during phase 1 of stimulation, a current stimulus 45 is delivered to the recipient via a stimulating contact (shown as electrode 35A) in intracochlear array 33. Stimulus 45 passes through the neural structures 44 and returns to the extracochlear electrode 11. This is the same as in a conventional implant. As shown in FIG. 2, stimulus 45 is represented by an arrow from electrode 11 to electrode 35A. This arrow is opposite to the flow of the positive charge of stimulus 45.

As described in greater detail below, in phase 1, ion switch 30 is "open" (i.e. has a high impedance). During phase 2 of stimulation, current flow 46 is reversed in polarity, and flows from electrode 35A in scala tympani 42 through silicone tube 31 and ion switch 30 to extracochlear electrode 11, bypassing neural structures 44. This is represented by the arrow extending from electrode 35A to electrode 11. In phase 2, ion switch 30 is "closed" (i.e. has low impedance).

Therefore, as schematically illustrated in FIG. 2, during the first phase the positive current flows from electrode 35A to the tissue, thereby crossing the electrode/tissue interface 41. The positive current then flows through structures 44 back to electrode. However, in the second phase, the negative current flows from electrode 35A to the tissue, again crossing the electrode/tissue interface 41. As a consequence, charge balance is preserved at the electrode/tissue interface 41. However, during this second phase, ion switch 30 and tubing 31 collectively provide a bypass pathway 18 for the return of negative current back to electrode 11. As such, the negative current does not flow across nerve structures 44 and therefore does not return the neural structures to their pre-phase 1 state.

The proximal and distal ends of silicone tube 31 are positioned to bypass the anatomy containing the neural elements to be stimulated, so that most or all of the phase 2 negative charge is not delivered to the neural structures. It will be understood that in practical applications, it is likely that some current will still flow through the neural structures in phase 2, but diversion of any negative current provides an improvement in efficiency. It is envisaged that in practical applications it may be desirable to reverse polarity from time to time. That is, instead of the desired stimulus being delivered as a positive pulse, a negative pulse is used, and vice versa in phase 2. This will assist in minimizing the effect of induced ion movement or ion imbalance.

Figure 5A:
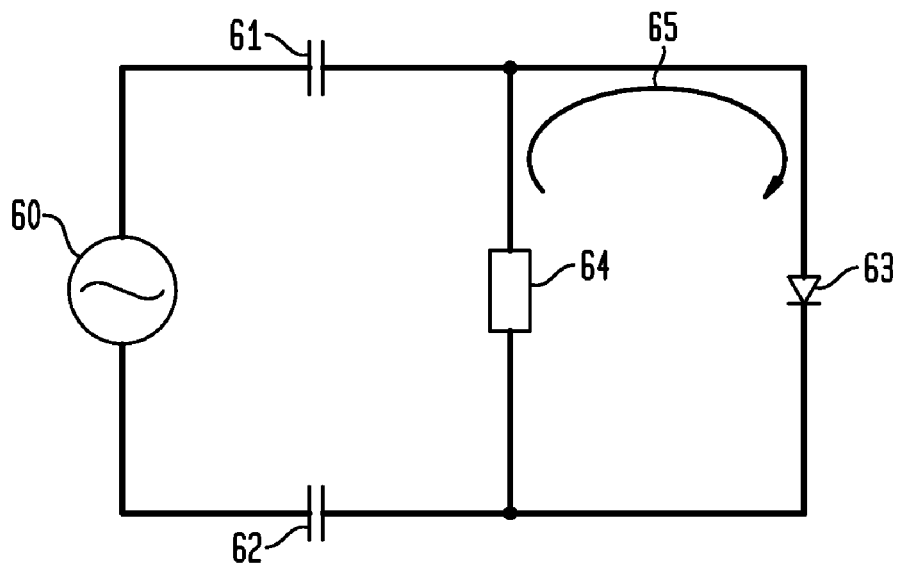
FIG. 5A schematically illustrates the principle of rectification using a diode.

This principle is similar to that of rectification of an alternating current (AC) to a direct current (DC), as illustrated in FIG. 5A. A non-linear circuit element, such as diode 63 can be used to rectify the AC. The AC source 60 generates an AC current, which is passed through the capacitors 61, 62. When the current is flowing in a first direction, from top to bottom on the page, both load 64 and diode 63 conduct. Assuming that the impedance of diode 63 in the forward direction is much smaller than the load, then most of the current passes through diode 63. When the current is reversed, from the bottom of the page to the top, then the diode will not conduct (i.e. prevents current flow in one direction), and all the current passes through the load. In one approach to rectification, known as a switched mode power supply, switches are selectively operated to provide the alternate current paths.

Figure 5B:
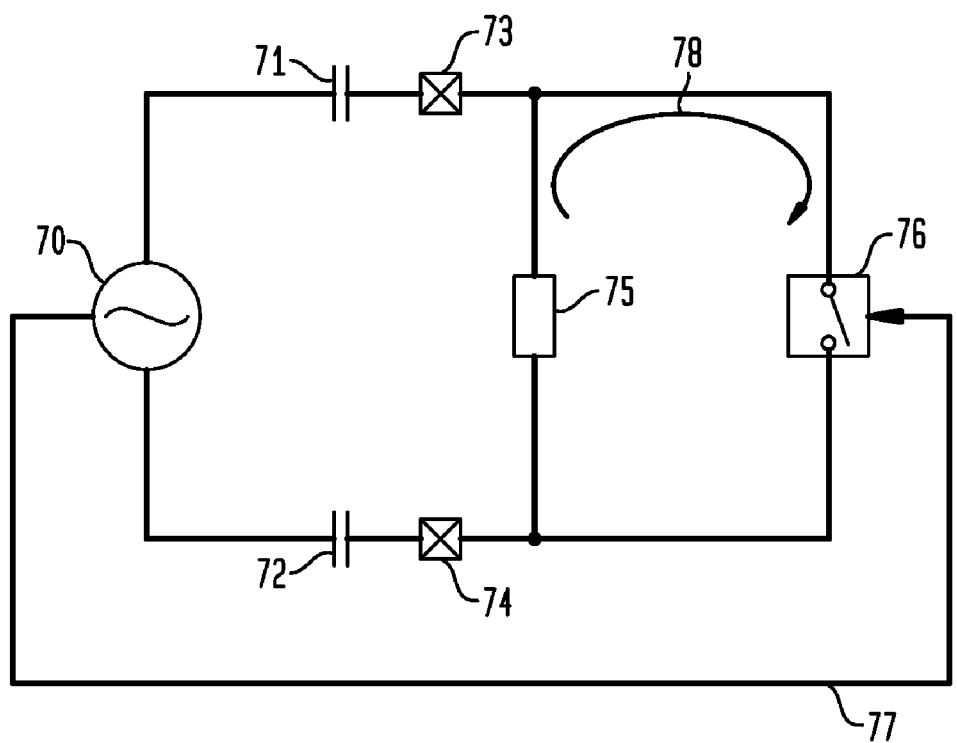
FIG. 5B schematically illustrates an ion switch acting as a diode.

The technique proposed according to the present invention for the example of a cochlear implant is illustrated in FIG. 5B in which ion switch 76 is substituted for diode 63, therefore acting as the non-linear element due to the timed control of the switch. This controlled switching creates the non-linearity so as to convert the AC into DC. Stimulator 70 provides an AC current that passes across capacitor 71, associated electrode 73, neural tissue and other parts of the body return path 75, through electrode 74, capacitor 72 and back to the stimulator. Ion switch 76 is operated so as to be closed (conduct current) with one phase, and be open and not conduct current in the other phase. As a consequence, the neural structures only receive substantially DC current.

In order to illustrate the operation of implementations of the present invention, following is a table that defines when the ion switches are open or closed in the implementation described in FIG. 1:

| Ion Switches . . . | Phase 1 | Phase 2 |
| --- | --- | --- |
| that permit current flow towards nerve | Open | Closed |
| that permit current flow away from nerve | Closed | Open |

As discussed above, it will be appreciated that if all the above switch positions are reversed, a net DC across the nerve in the opposite polarity is achieved. DC in either polarity may be advantageous.

It would be appreciated different devices may achieve substantially the same function as an ion switch, and different devices may be used for different applications. The essential function of such devices is to selectively increase or decrease the impedance of an ionic conduction path, so as to allow different current directions to be switched along different paths. Any suitable device which can achieve this function, at an appropriate speed for the rate of stimulation, may be employed. The examples provided herein are purely illustrative, and are nor intended to be limiting.

For example, in an alternative embodiment, the ion switch may be replaced within an ion permeable membrane that only allows the flow of ions in one direction. In such an alternative, said the ion permeable membrane would be arranged to completely or substantially cover a cross-section of the silicone tube 31 (FIG. 1) at one point along its length. Such a membrane has a similar effect on the currents flowing in phases one and two of the biphasic current signal as the ion switch. In another embodiment, a mechanical arrangement may be used to physically occlude a tube containing a conductive fluid, such as a body fluid. The detail of possible ion switch structures will be further discussed below.

Figure 15:
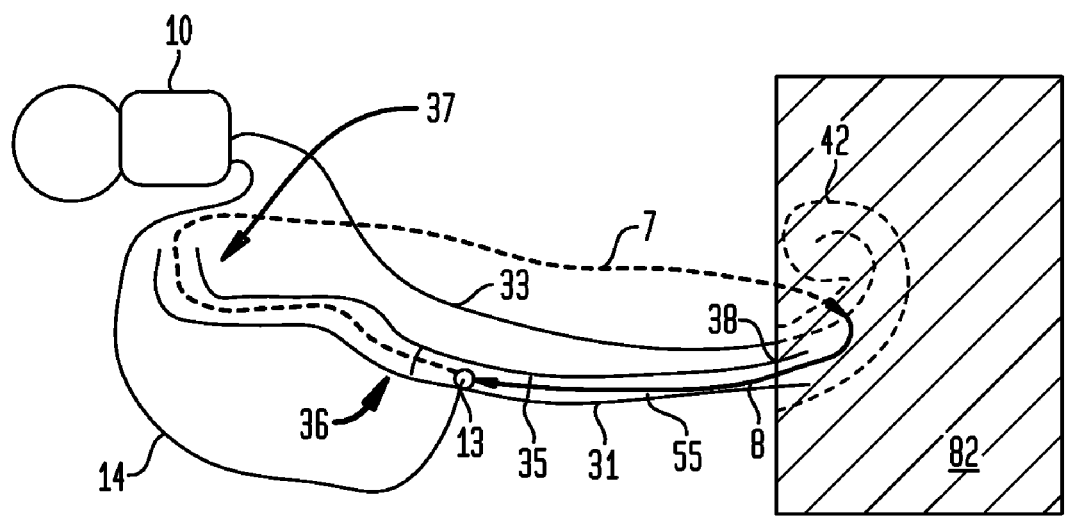
FIG. 15 is a conceptual diagram illustrating a cochlear implant, in accordance with further embodiments of the present invention.

FIG. 15 illustrates an alternative implementation of a system that incorporates two ion switches 35, 36 in a bypass pathway to achieve more efficient rectification of the ion current. In this implementation, receiver stimulator 10 and electrode array 33 are provided as in the implementation of FIG. 1. Silicone tube 31 is also provided, with one end opening adjacent to receiver stimulator 10, and the other end opening into the scala tympani 42. However, in this implementation, the extracochlear electrode 13 is located within the silicone tube 13, with ion switch S1 36 disposed on one side, and ion switch S2 35 disposed on the other side of electrode 13. Extracochlear electrode 13 is connected via an insulated lead 14 to the receiver stimulator unit. Thus, the extracochlear electrode 13 is located between switches S1 and S2 within tube 31.

Following is a table outlining switch timing for this implementation:

| Switch | Phase 1 | Phase 2 |
| --- | --- | --- |
| S1 | Open | Closed |
| S2 | Closed | Open |

During phase 1 of stimulation in accordance with the embodiments of FIG. 15, ion switch S1 is open and S2 is closed. The stimulator circuitry passes stimulation current between an intracochlear electrode (not shown) in array 33 and extracochlear electrode 13. Because S1 is open and S2 is closed, current is directed from extracochlear electrode 13 to the opening 37 of the tube near the implant body, which is in a similar location to the extracochlear electrode in a conventional cochlear implant. From there the current follows a conventional path through tissue to the intracochlear electrode in array 33. Thus the current path through tissue during phase 1 is more or less the same as it would be for a conventional cochlear implant stimulator, and is shown as arrow 7. During phase 2, S1 is closed and S2 is open, and current flows from the intracochlear electrode in array 33, to the opening 38 of the tube within the scala tympani 42, and then down the ionic fluid 55 within tube 31 to extracochlear electrode 13. This is a different current path from the conventional one and largely bypasses the nerve tissue, so that the nerve sees a largely monophasic current waveform. This path is illustrated by arrow 8.

Figure 3:
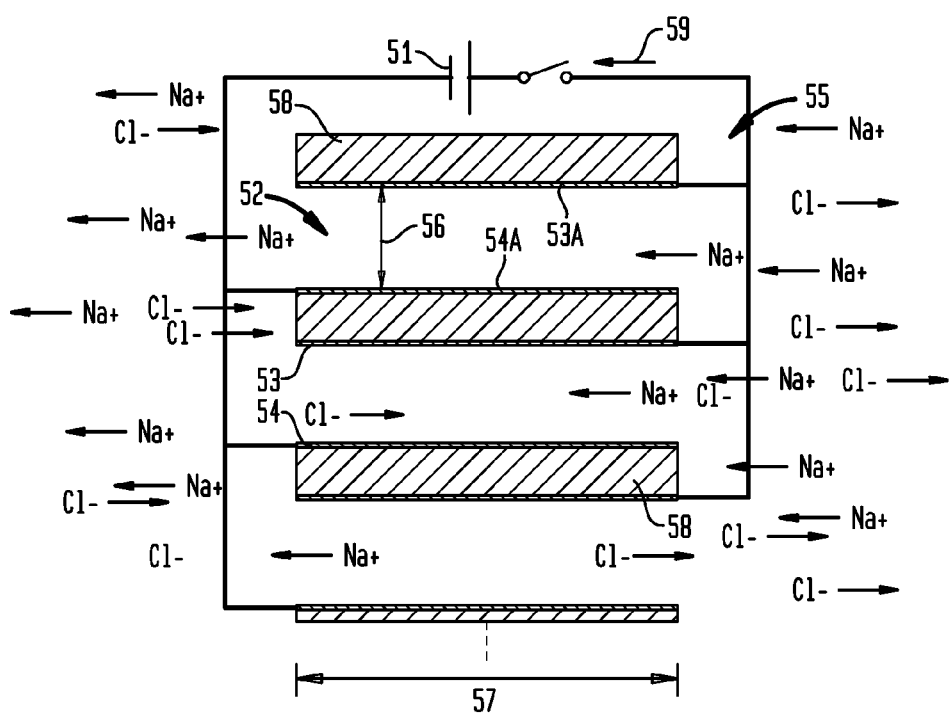
FIG. 3 is a schematic sectional view of an open ion switch, in accordance with embodiments of the present invention.
Figure 4:
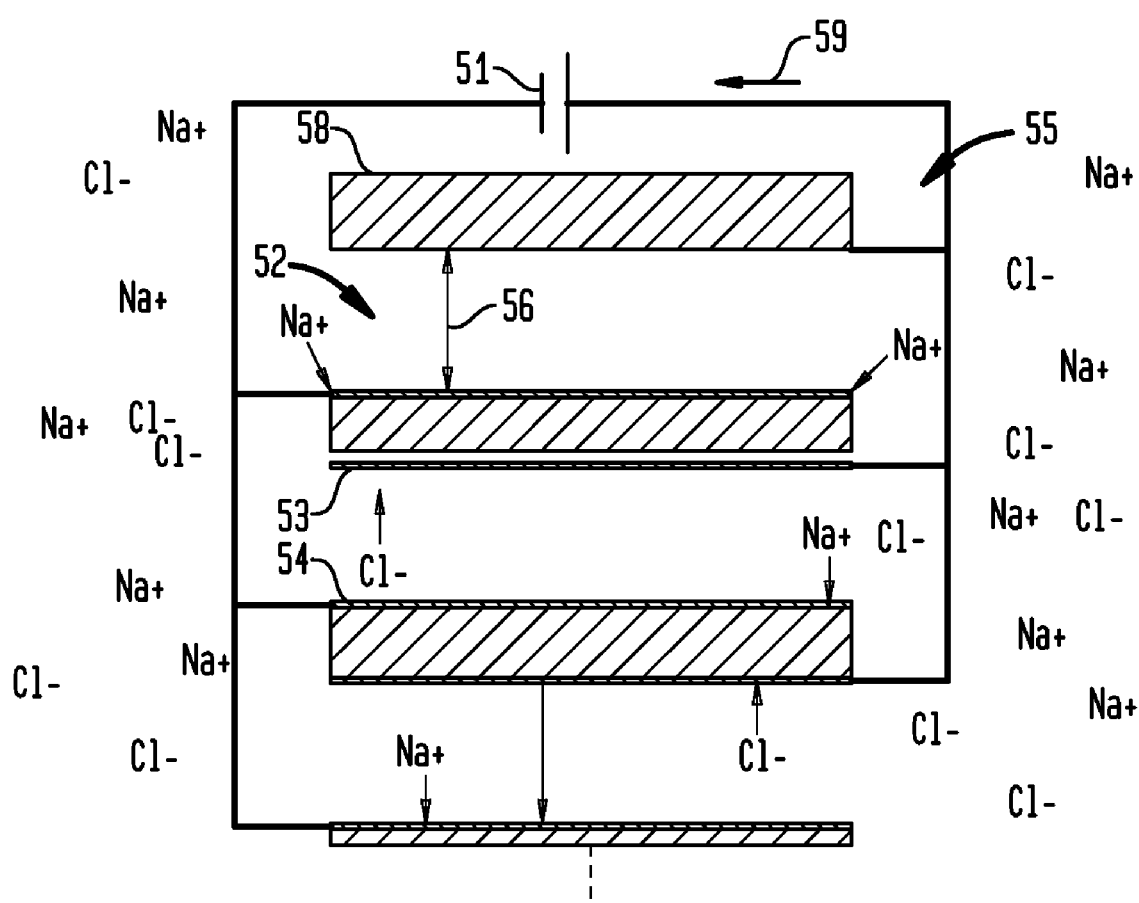
FIG. 4 is a schematic sectional view of the ion switch of FIG. 3, shown in the closed position.

FIGS. 3 and 4 illustrate a section of one implementation of an ion switch that may be used in embodiments of the present invention to change the mobility of ions flowing through it. Small channels 52 having a width 56 (are constructed through a substrate material 58, so that the channels have a length that is substantially large relative to width 56. Width 56 is selected to be substantially less than the diffusion length of the ions that will pass through the switch. Opposite sides of the channels 52 are lined with platinum or other inert metal electrodes 53, 54, 53A, 54A. Each of the sets of electrodes 53, 54, 53A, 54A across each channel 52 is connected to different polarities, provided by DC source 51 and control switch 59. The ionic fluid 55 contains ions, such as, for example, sodium and chlorine. FIG. 4 illustrates the 'on' situation when a control voltage is placed across the electrodes. Ions are attracted to the respectively charged plates (negative ions to one plate, positive ions to the other) and their mobility decreases dramatically. This acts to decrease the impedance through the switch. In a typical application the channel widths would be a few microns and multiple, parallel channels would be constructed to reduce the "on" impedance of the switch to a reasonably low value. It will be appreciated that it is preferable that the on impedance be as low as possible. FIG. 3 illustrates the situation when no control voltage is applied across the electrode, (i.e. they are at equal potential) and the ions are free to flow in the channel with their normal mobility.

In practice, because of the non-zero impedance of the ion switch path and the non-ideal placement of the tube ends, some of the paths will be shared by both phases. The more independent the paths between the two phases are, the more benefits will be gained.

Figure 6:
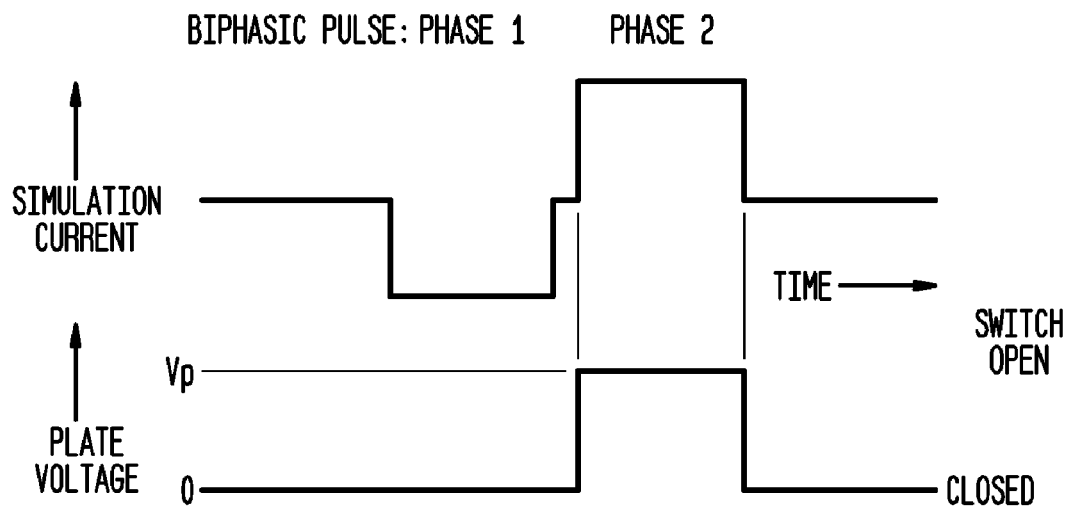
FIG. 6 is a timing diagram illustrating operation of the ion switch relative to the stimulation current.

In the example of FIG. 1, the control line(s) 34 are used to close ion switch 30 during all times other than phase 2 of the biphasic current signal, and then to open the ion switch only during phase 2. FIG. 6 schematically illustrates the timing of the switch (plate) voltage, relative to the stimulation current. As noted above, the selection of phase 2 to close the ion switch is somewhat arbitrary, as a similar effect could be produced by closing the ion switch during only phase 1. That is, DC can be delivered across the nerve in either direction (either DC current flowing in the direction of phase 1 OR DC current flowing in the direction of phase 2). This is achieved by changing the timing of when the ion switch is open/closed. If it is open during phase 1 and closed during phase 2, the net DC across the nerve will be induced in the direction of phase 2. If it is open during phase 2 and closed during phase 1, the net DC across the nerve will be induced in the direction of phase 1.

For non-biphasic stimuli, a similar effect can be achieved by closing the ion switch only when the current is in one particular polarity. It may be desired to apply stimulation current simultaneously from more than one electrode (also known as simultaneous stimulation), for example at different locations in the cochlea. Simultaneous stimulation is also possible using the approach of this implementation, provided that the second phases of the simultaneously applied pulses are aligned in time. The ion switch can be opened during the time when all the phase 2s are being applied to achieve the desired effect.

It will be appreciated that the specific implementations of ion switches described herein are merely illustrative, and that embodiments of the present invention may be implemented with any suitable structure that may provide the required controlled ion switching. Apart from the functional criteria that the ion switch regulate impedance, it is also preferably low power, small, fast and biocompatible. The control signals for this ion switch should be of the order of a few hundred mV or less to avoid significant power losses in the switching itself. Current may flow between the switch electrodes if this voltage is exceeded. The required voltage is a function of the distance between the plates as it is the field in the ionic solution that attracts ions to the plates and increases their mobility.

Since the distance between the plates can be made to be very small, it is possible to achieve the required fields within the required voltages. In order to minimize the impedance, it is necessary to maximize the area of the switch electrodes. It is also important to have regard to the geometry, and speeds, so as to understand the effects of ion diffusion from outside the switch on the effectiveness of any induced ion movement changes within the switch.

It will be understood that a variety of possible geometries and arrangements can be used to create an electrically controlled ion switch. For example, one implementation may use a rolled up foil, similar to an electrolytic capacitor. For a 100 nm gap, 2 mm deep foil, 14 m of foil breadth is required.

Another possible implementation is a metal plate with orifices formed through it, with the potential applied between the plate and the solution. It is also noted that it would be possible to operate the ion switches in a cascaded way in a suitable implementation, so an array of successive switches is more effective than each switch alone.

The control signals for the ion switches should be AC coupled (i.e. pass no DC) to avoid problems with by-product production at the interface between the plates and the ion channels. This may be achieved, for example, by driving the control signals through a series capacitor to remove any DC component.

As noted above, embodiments of the present invention utilize a silicone tube as part of the bypass pathway. In certain embodiments, the silicone tune provides as low impedance a path as possible from end to end. However, it should be appreciated that any bypass impedance path that can be switched to a higher or lower impedance at the appropriate times will change the amount of current flowing through the neural elements, and will therefore potentially improve the efficiency of stimulation. If the total bypass impedance of the pathway (tubes plus switches) is zero, the pathway it will conduct all current around the neural elements during one phase of stimulation. To be practically useful, the bypass impedance with the switch in the "on" state must be of the same order of magnitude or lower than the impedance of the path without the silicone tube in place. It will be appreciated that even a partially effective bypass mechanism will be useful, as it will reduce the amount of negative charge delivered to the neural structures.

The tubes of the bypass pathway may, in certain embodiments, be initially be filled with an ionic solution similar in composition to that of extracellular fluid. In other embodiments, ionic solution is not used and the tube fills with body fluid and diffusion ensures that the concentration of ions becomes the same inside and outside the tube. To avoid the tubes filling up with tissue, barriers may be inserted at the ends of the tubes exposed to body fluids. Such barriers may, for example, provide a selectively permeable barrier that is permeable to ions but not to cells. The ion switch itself can be used in this capacity and can be placed at the end of the tube to prevent the intrusion of cells into the tube. The preferred channel diameter within the ion switch is sufficiently small that cells cannot pass through the channels.

Embodiments of the present invention have been mainly discussed with reference to a particular tube placement noted above. It would be appreciated that there are many different places the tube ends could be placed to provide a reduced impedance path that partially or fully bypasses the stimulatable neural elements. In one arrangement, one end of the tube is in the perilymph and the other ends is on the other end of the auditory nerve, for example, near the auditory brainstem. In embodiments, the tube ends bypass that part of the current path that caused current to flow over the nerve. For other neural stimulators, it is important to take account of the nature and path of current flows when considering how to locate the bypass tube.

The tube needs to be of adequate diameter to allow sufficient ion transport such that the impedance is substantially lower when the switch is operative than the alternate paths. A typical tube might have a diameter at one end of approximately 2 mm (to allow it to fit in the cochleostomy) and then widen to approximately 5-10 mm for the rest of its length, thereby minimizing the overall impedance. The length is governed by the distance of the path between the cochlea and the extracochlear electrode which may be approximately 10 cm. In certain embodiments of the present invention, the tube may be partially or fully incorporated into the existing electrode array structure that already passes from the cochlea back to the stimulator. The tube may be formed from any suitable insulating, biocompatible material. In certain embodiments, the tube is formed from flexible material, having sufficient strength to resist compression forces and remain open against the normal forces within the body, and associated with movement, etc. The tube may have any suitable cross sectional shape, or be variable in shape if appropriate.

Figure 7:
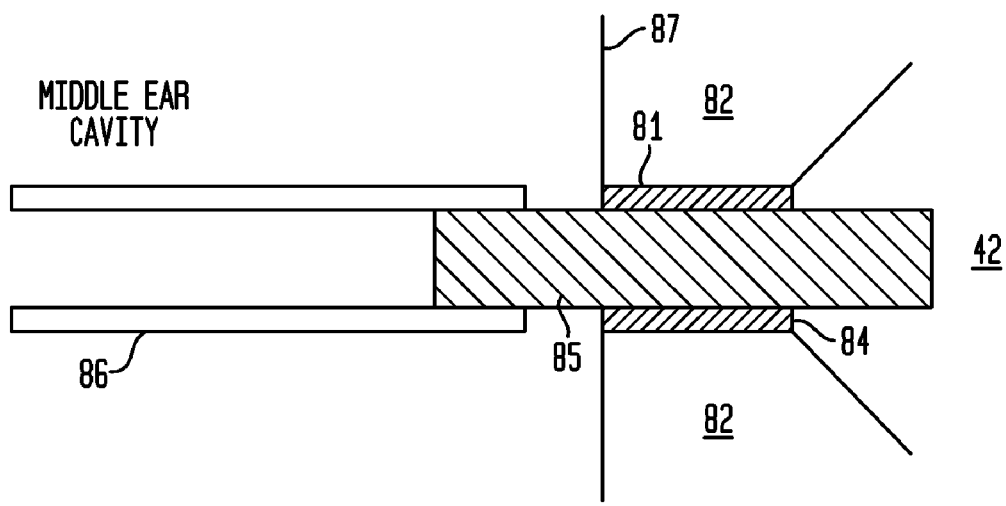
FIG. 7 is a sectional view illustrating embodiments of the present invention having a tube communicating with the scala tympani via a porous material.

As an alternative to placing the tube end within the cochlea, the end of the tube could be placed on the middle ear side of the cochleostomy. To assist with current conduction through the cochleostomy it may be possible to place a solid rod of material porous to ions through the cochleostomy. The pore size would be large enough for ions to flow and small enough to prevent microbes from flowing (e.g. 1 µm diameter). FIG. 7 illustrates one such exemplary arrangement in accordance with embodiments of the present invention. As shown, tube 86 fits over the end of porous rod 85. Porous rod 85 extends through the cochleostomy 81 from the middle ear cavity 80 to the scala tympani 42. Bone 82 and scar tissue 84 surround the rod, to operatively hold it in position. The rod 85 provide a conductive path, but without a tube being in contact direct contact with the perilymph.

Another alternative would be to use a conductive wick structure rather than an open tube to conduct the current through the air filled cavity of the middle ear. The wick would have the advantage that there would be no danger of biofilms forming within the tube as the wick would be open to the air of the middle ear cavity. The disadvantage is that the wick is only able to conduct DC current when it becomes impregnated with tissue since the DC flow must be ionic and tissue provides this medium. In another embodiment, artificial tissue could be used, for example a structure which was essentially a porous scaffold that trapped ionic solution thus making it conductive. Another alternative is to use a tube with a slit along its length. The tube would largely contain the current within its boundaries through the middle ear cavity and the slit would allow access between the middle ear and the inside of the tube, preventing entrapment of biofilms.

Figure 8:
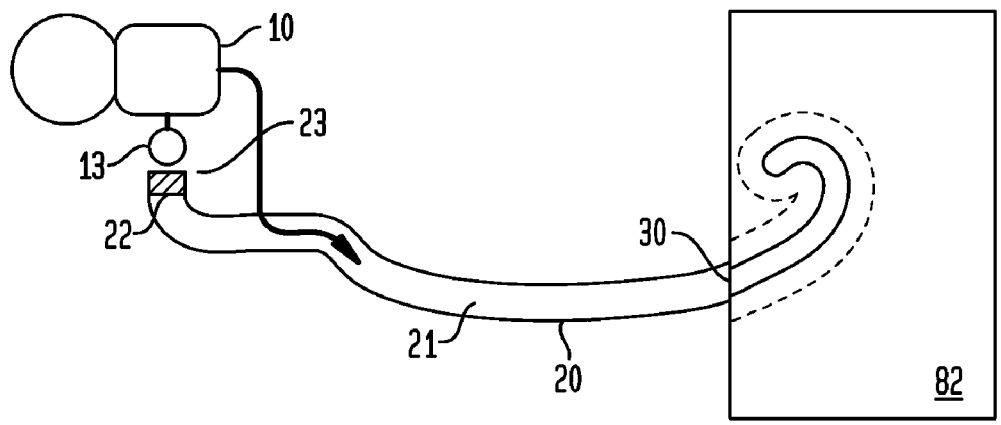
FIG. 8 is a conceptual view of a cochlear implant, in accordance with embodiments of the present invention.
Figure 9:
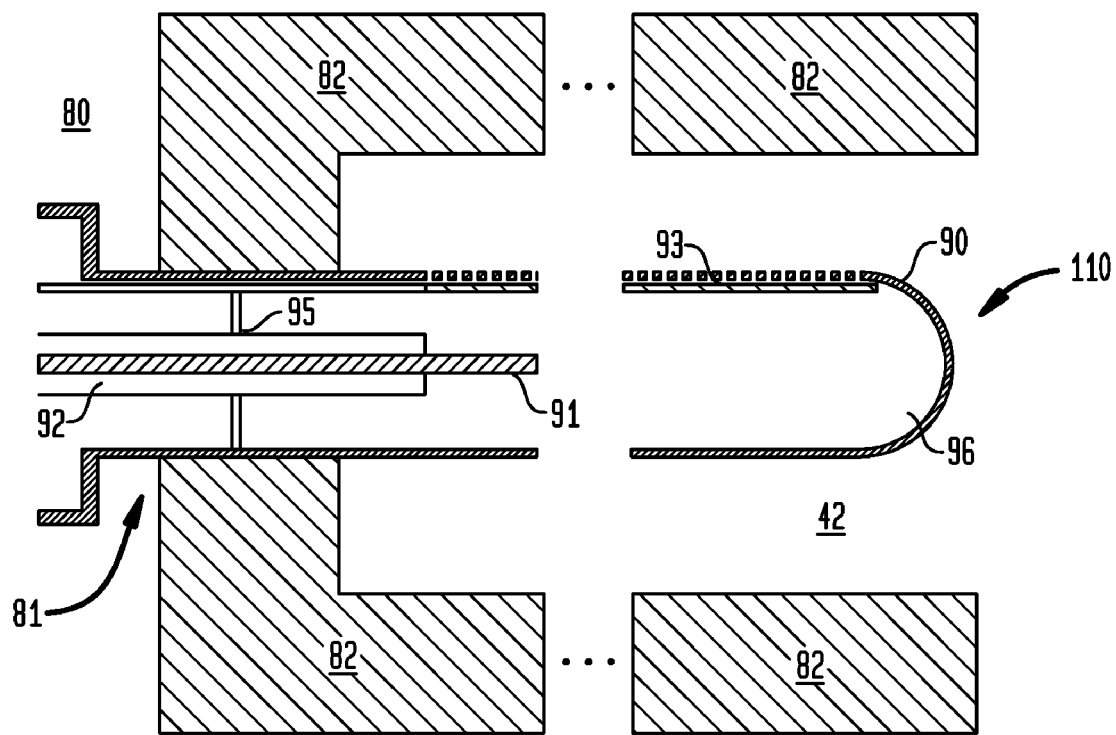
FIG. 9 is a sectional view of the cochlear implant of FIG. 8.
Figure 10:
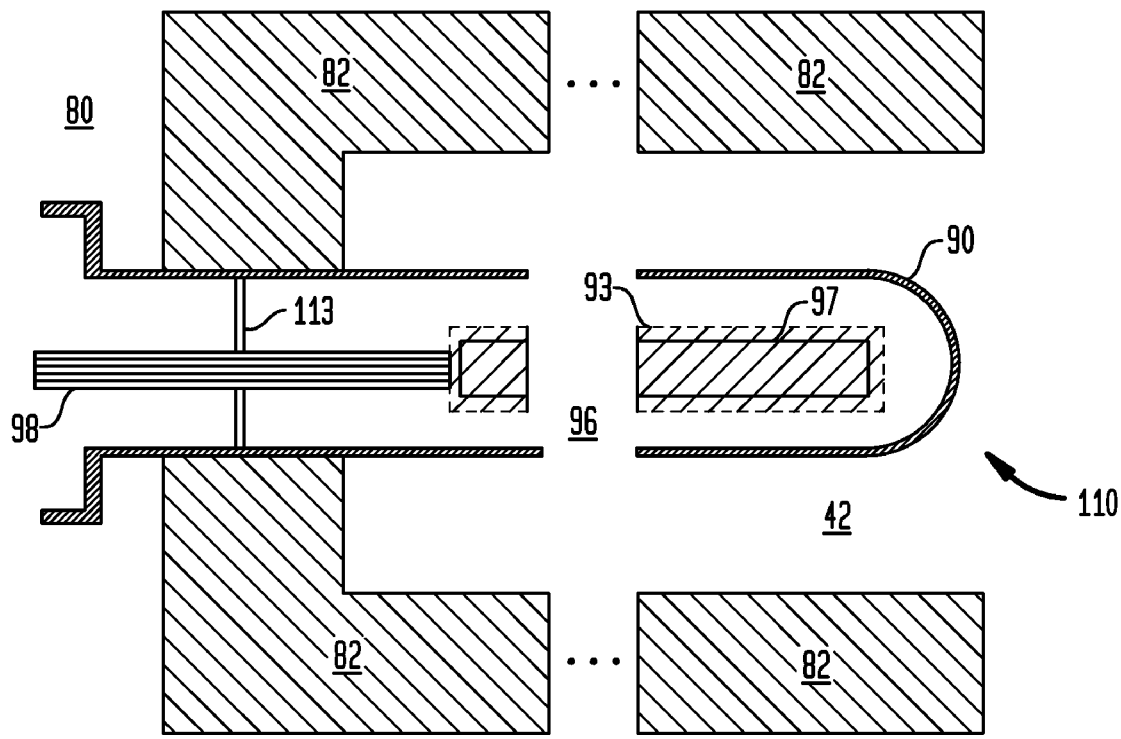
FIG. 10 is a schematic top view of the cochlear implant of FIG. 9.

A possible issue relating to the present invention is concerned with impedance. In general, the DC impedance of tissue is higher than the AC impedance, as current has to flow through the spaces between cells rather than through or across the cell walls. Since FIGS. 8, 9 and 10 shows an overall view of an alternative implementation of the present invention. The key difference from the implementation of FIG. 1 is that the ion switches are incorporated into the electrode array, rather than having them outside the cochlea and independent of the array.

Referring first to FIG. 8, the electrode array is located inside an insulating tube 20, filled with ionic fluid 21. At the cochleostomy, an additional ion switch 30 is provided. One end 23 of the tube, adjacent to the receiver stimulator unit 10, opens near the extracochlear electrode 13. Optionally, a barrier material 22 may be provided to prevent the ingress of bacteria and other cells, but allow the passage of ions.

FIGS. 9 and 10 show a cross-section and plan view respectively of part of the intracochlear electrode array of FIG. 8. It will be appreciated that the array is illustrated as being of indefinite length. The intracochlear electrode array 110 is contained within an insulating enclosure 90 and includes stimulating contacts in the form of an ion switch array 93, replacing the multiple electrodes of a conventional multi-electrode array. A single metal electrode 96 is disposed inside the ion switch array 93. As such, rather than using electrode locations as in conventional devices, ion switches of array 93 operate to direct the current flow. This allows all current flow out of the intracochlear array 110 to be completely stopped (by closing all the switches, assuming that they have very large impedance when open) so that current can be directed out of array 110 and to extracochlear electrode 13 via insulating tube 20. The tube contains ionic fluid from the surrounding perilymph. Each individual ion switch can be controlled in a similar manner to the individual electrodes of a conventional array.

For existing metal electrodes used in neural stimulator applications, the maximum charge density (charge per unit area of electrode surface) is limited to avoid corrosion and harmful by-product generation. Therefore in practice the minimum electrode area is limited to approximately half a square millimeter. No such limitation exists with ion switches. Additionally, ion switches may be made very small, so that very fine spatial control of current flows becomes possible. The metal electrode in this implementation is very large, so that large charges can be passed without charge density issues. This minimum intracochlear electrode size limit is already a significant restriction on current generation cochlear implants. As the ion switch is not a metal/tissue interface, this issue is avoided.

In embodiments of the present invention, the ion switches provide the localization, and the current source (that provides current between the intracochlear and extracochlear electrodes) controls the current that is delivered. As such, if 1 mA is required to be delivered at position 22 in the cochlea, then in phase 1, 1 mA is passed between the electrodes and at the same time the ion switch at position 22 is opened. During phase 2, 1 mA is passed in the opposite direction and all intracochlear ion switches are closed. It will be appreciated that close co-ordination between the ion switches and the current source is important to such embodiments.

Ion switch 30 is located inside the insulating electrode tube at the cochleostomy and serves to prevent current flowing out of the cochlea when stimulation current from the intracochlear electrode 96 is flowing. As such, in the first phase of the biphasic pulse, the intracochlear ion switches are open, the cochleostomy switch is closed and all current flows in the normal way from the intracochlear electrode through one or more ion switches to an extracochlear electrode. In the second (opposite polarity) phase of the stimulus pulse pair, the cochleostomy ion switch is opened and the ion switches within the intracochlear array 110 are closed. All the stimulus current in this phase is therefore forced out of the cochlea and into the extracochlear electrode through the insulating tube 20 without flowing across the nerve. This is a more electrically efficient implementation than that of FIG. 1, since the use of the ion switches in the intracochlear array almost completely blocks the flow of current across the nerve in phase 2. The implementation of FIG. 1 provides a combination of AC and DC to the nerve in a practical application, as not all the current will pass through the diversion structure.

Figure 11:
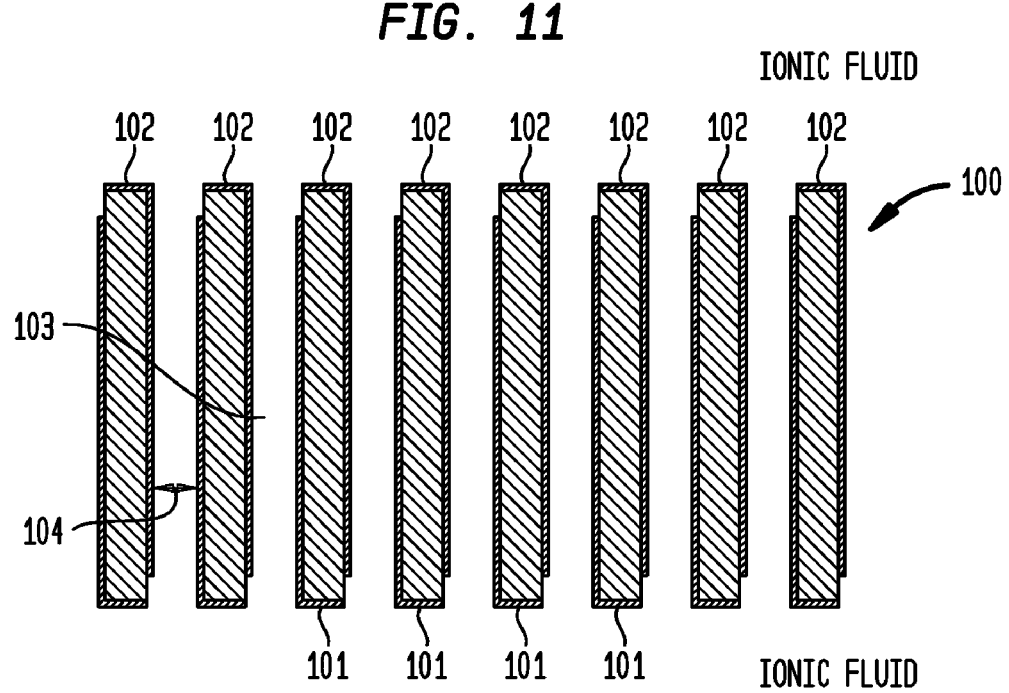
FIG. 11 is a detailed view of the ion switch implemented in the embodiments of FIGS. 9 and 10.
Figure 12:
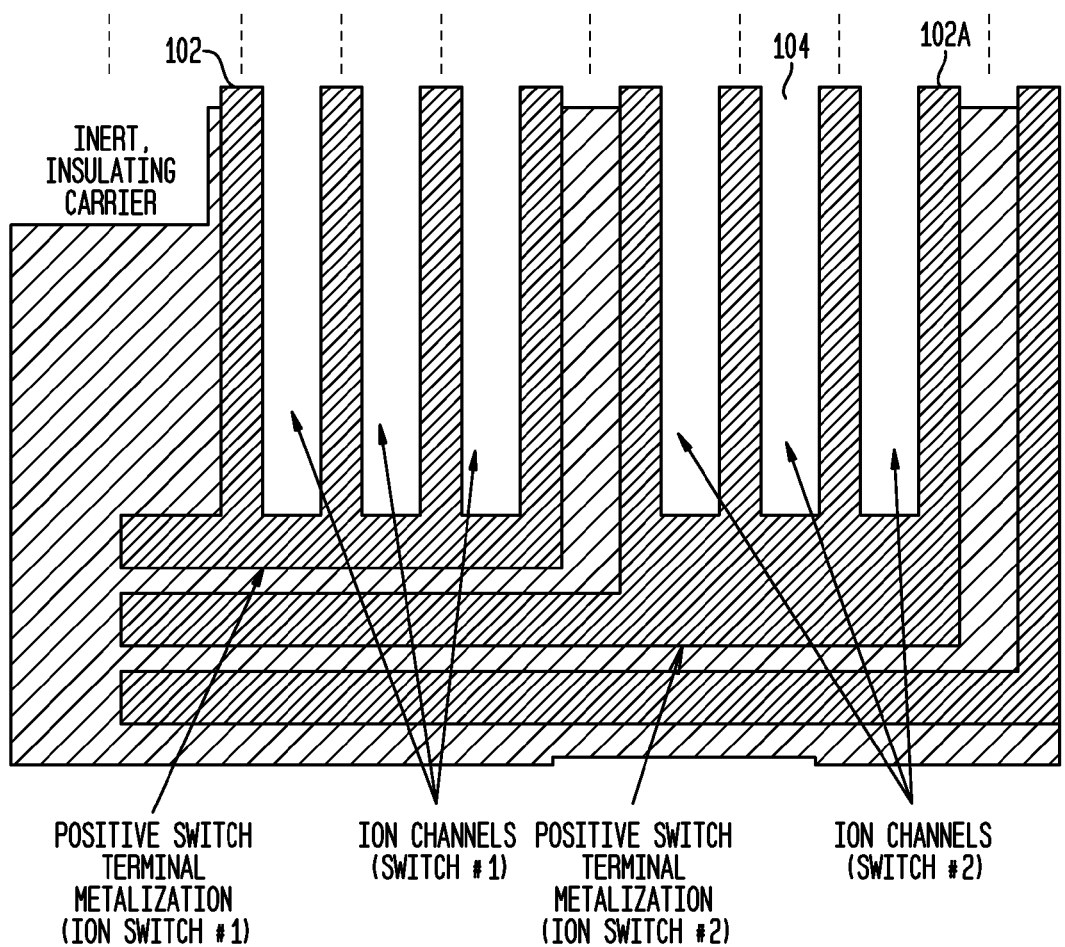
FIG. 12 illustrates one construction for an ion switch array, in accordance with embodiments of the present invention.

As shown in FIG. 8, the proximal end of tube 23 is placed close to extracochlear electrode 13. In an alternative embodiment, tube 23 completely surrounds extracochlear electrode 13, and an ion switch (not shown) is inserted into the tube close to electrode 13. In this case the ion switch near extracochlear electrode 13 would be opened during phase 1 of the stimulation to allow current to flow to the extracochlear electrode, and then be closed during phase 2 of the stimulation to confine the return path of the current to the tube. This method can be used either with or without the ion switches incorporated into the intracochlear portion of the electrode array as shown in FIG. 9. As previously noted, the use of multiple switches may serve to increase the change in impedance provided by opening and closing the switches. FIGS. 11 and 12 show an expanded view of part of an example construction of an ion switch. In embodiments of the present invention, an ion switch has channels of no more than a few microns in width (i.e. less than the diffusion length of the ions in question), with conducting electrodes placed on either side of the channel. In one example, an inert substrate creates channels with positive electrodes 102 on one side, and negative electrode on the other side 101. Each channel defines a different switch in the array. FIG. 12 is a plan view illustrating separate connections for each switch, which may be one or a small group of channel, are provided. When no potential difference is applied across the electrodes, floating ions are free to flow through the channel and the switch is effectively "on". If a potential is induced between the plates, ions are attracted to one or the other of the plates (positive ions to the negative plate, negative ions to the positive plate). This prevents them from flowing through the channel and the switch turns "off<1>. There are many ways in which numerous, small channels, flanked by metallised electrodes, can be constructed. Current microfabrication techniques may favour alternative construction methods.

Figure 13:
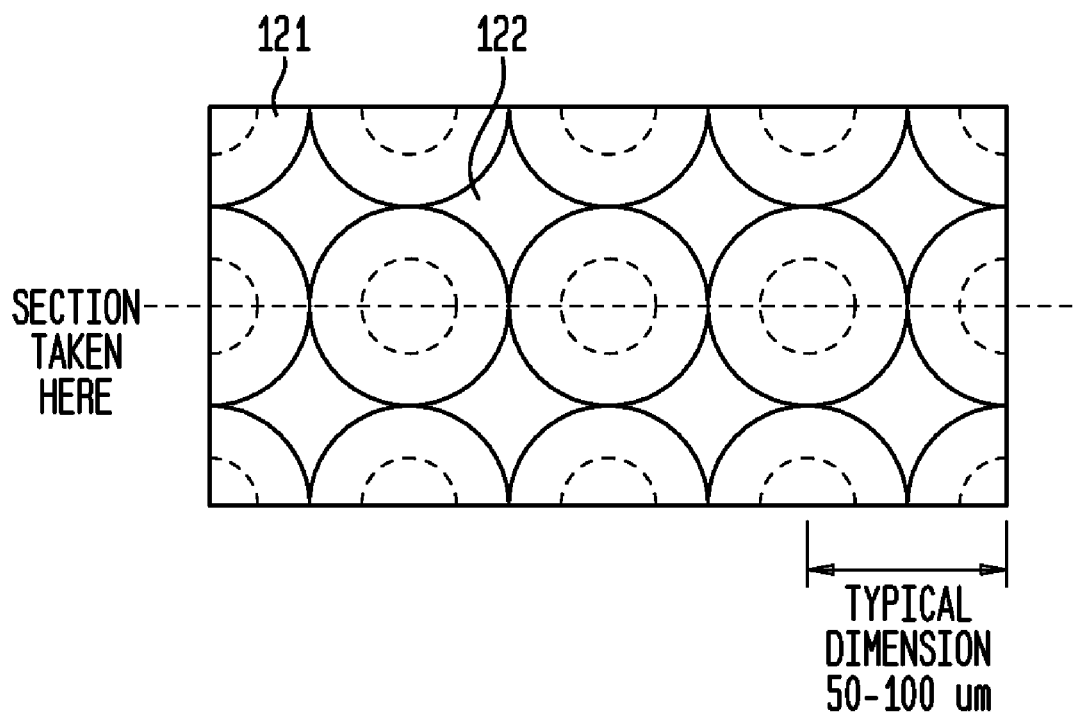
FIG. 13 is a plan view of an alternative ion switch array construction, in accordance with embodiments of the present invention.
Figure 14:
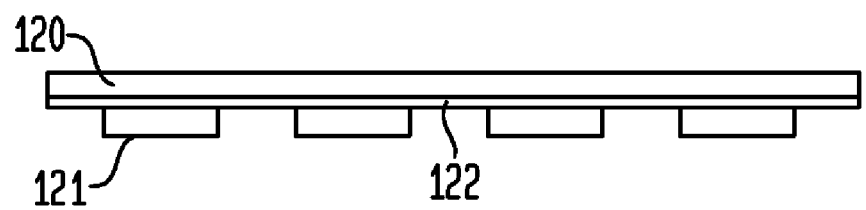
FIG. 14 is a sectional view of the array construction of FIG. 13.

FIGS. 13 and 14 show an alternative type of ion switch that may be used in embodiments of the present invention. In these embodiments, the switch is formed from two layers of metal, a top plate 120 and a bottom plate 121, and has an intervening porous separating layer 122. The separating layer 122 needs to be nonconducting, but porous to ions. It may be, for example, about 1 micron thick. The top and bottom metal layers may be formed from any suitable biocompatible, non reactive material, for example a platinum alloy.

Holes are formed in both the top and bottom layers, but in a non overlapping manner, so that ions pass through one of the layers, through the porous material laterally. The ions then pass through a hole in the other layer. In this arrangement, the top plate 120 and bottom plate 121 are conductively connected together, and the ion gates are controlled by applying a potential to selected bottom plate sections, each of which has a corresponding connection to the stimulation device. This arrangement is used with an electrode structure otherwise similar to FIGS. 9 and 10.

In the system described in FIGS. 9 and 10, the control of where the current flows in the cochlea is determined by electrical control signals that run to the ion gates. Each of these control signals use a current that is lower than the stimulus currents that are used in a conventional, existing electrode array. Therefore, additional wires may be used, allowing potentially hundreds of individually controllable ion gates to be used. This is because one of the existing limitations on the number of electrodes in a conventional electrode array is the minimum limit on the wire thickness. If the wire is made too thin, the resistance increases and ohmic losses become significant. With lower currents, this is a much smaller issue, and hence potentially hundreds of control wires can be passed into the cochlea rather than a few tens of wires as is the limit for conventional technology, without the actual dimensions of the wire bundle increasing correspondingly. This implementation provides the ability to safely pass almost pure DC across the nerve, leading to very efficient stimulation. While current is passed in positive polarity, one or more of the ion gates within the cochlea are open and the ion gate within the electrode array (that connects it to the extracochlear electrode) is closed. This passes all positive current into the cochlea as desired. When negative current is passed, all the ion gates within the cochlea are closed and the ion gate connecting the inside of the array to the extracochlear electrode is open. In this mode all the current is passed to the extracochlear electrode and none flows in the cochlea. This is more efficient than the previously described implementation of FIG. 1 where some current in the negative polarity could still flow to the nerve.

Figure 16:
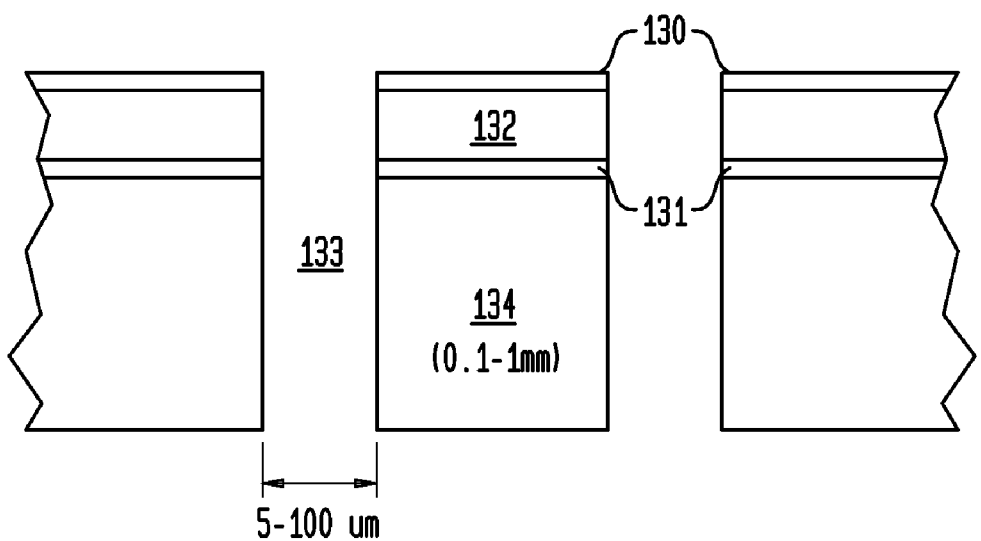
FIG. 16 is a sectional view of another alternative ion switch construction, in accordance with embodiments of the present invention.

Another alternative construction for the ion switches in accordance with embodiments of the present invention is shown in FIG. 16. In this implementation, metallization may surround the top and bottom of the channels as shown in FIG. 16. A top metal plate 130 and bottom metal plate 131 are separated by an insulator 132. The assembly is supported by a larger layer of insulator 134. Ion channels are formed through the structure 133. The dimensions of the ion holes may be in the region of 5 μm and the separation of the metalized plates may be in the region of 100 μm. These dimensions may be achieved by laser cutting of conventional insulator sheets with suitable metal layers provided on both sides. FIG. 16 also shows the bonding of a thicker layer of insulator 134 to the ion switch metal/insulator/metal prior to cutting the laser holes. In this way the ion switch insulator and metal plates can be made thin (to achieve high field strength and more efficient electrical operation of the switch) while the base insulator can be made thick (to provide strength) without compromising the electrical operation of the switch.

All manner of hole shapes, sizes and density are possible. The holes could be circular or square or any suitable shape. Additionally, ion transfer mechanisms are designed having regard to the effects of ion flow on the function of structures. If the concentration of ions at either end of the tube is markedly different, then this will result in an exchange of ions which may be unhealthy for the body. This can be overcome by reversing the polarity of phases one and two of the stimulation, for example every few minutes (or after a time long enough to allow the benefits of DC nerve stimulation to apply but short enough to prevent significant change in ionic concentration).

The embodiments as described in FIGS. 9 and 10 is ideal for stimulation using sequential monopolar stimulation, as previously described. Other modes of stimulation can also be achieved. Simultaneous stimulation can be achieved by opening more than one intracochlear ion switch simultaneously. In this configuration the currents flowing through each ion switch cannot be individually controlled (only the total current can be controlled). However, the relative times during which the switches are open can be controlled, so this allows individual control of the charge conducted by each ion switch, providing a method of controlled simultaneous stimulation. Bipolar stimulation (between two intracochlear ion switches) cannot be applied with the system described here. However, by having two individual, ion switch-based arrays, each similar to the one described here, inserted into the cochlea, bipolar stimulation could be applied by passing current between an ion switch on one array and an ion switch on the other array. In practice the two ion switch arrays may be mechanically connected or formed in a single piece. This is because a single member is easier to insert and avoids the possibility of biofilm formation between two closely adjacent foreign surfaces.

Figure 17:
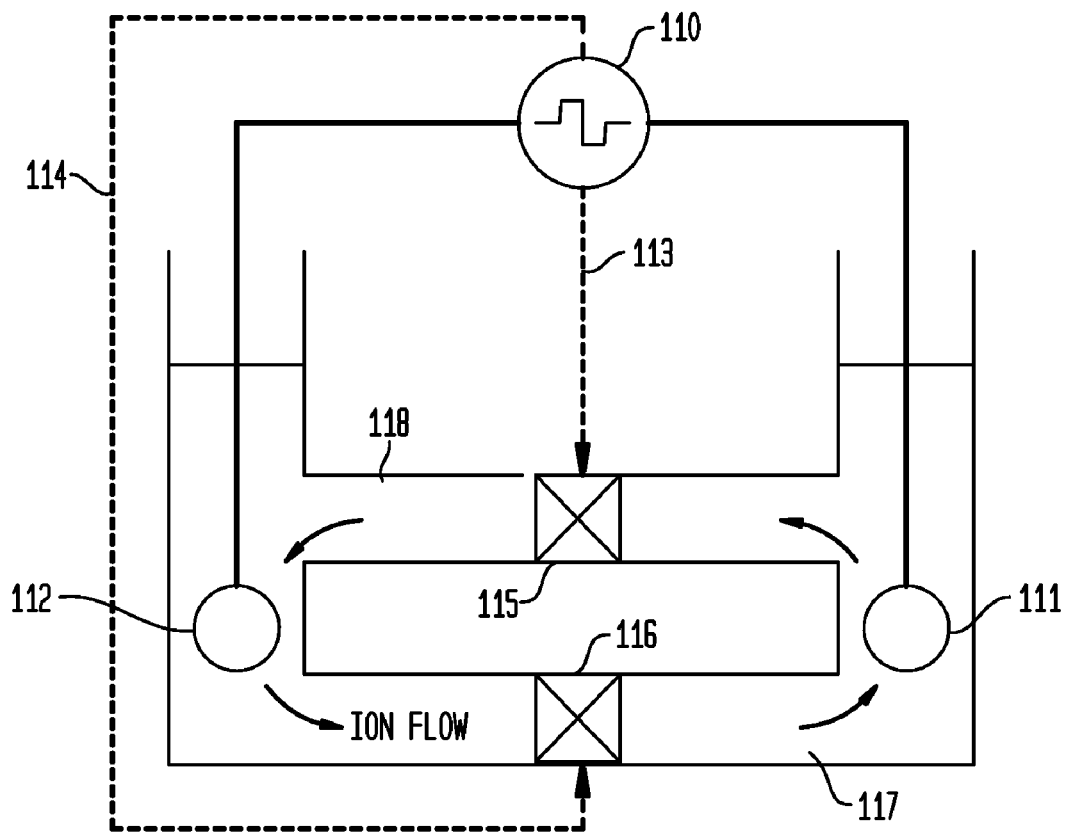
FIG. 17 is a schematic view of the operation of a mechanical type of ion switch system, in accordance with embodiments of the present invention.
Figure 18:
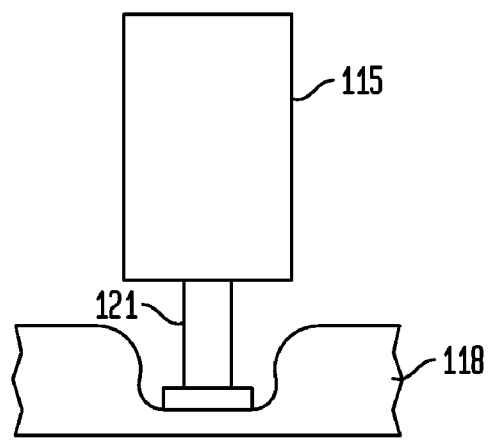
FIG. 18 is a view of a mechanical ion switch, in accordance with embodiments of the present invention.

FIGS. 17 and 18 illustrate embodiments of the present invention suitable for use with a stimulator that has a relatively slower rate of stimulation. In this arrangement, AC current source 110 is used to provide stimulation across two electrodes 111, 112, although the same principle could be used for a more complex electrode arrangement. This may be any type of stimulation, for example spinal chord stimulation.

The current passes between electrodes 111, 112 through the ionic fluid 117. By controlling the mechanical valves 115, 116, it can be seen that the current can pass through the selected path 117, so as to create the desired stimulus polarity in one phase, and use the alternate path to pass the opposite polarity using a different conduction path. Valves are controlled by control signals 113, 114. This may be implemented with any suitable valve arrangement, which is effective to block the conduction path.

FIG. 18 illustrates one possible implementation. Actuator 115 operates external to the flexible tube 118, so as to compress the tube and create a blockage, thereby preventing or at least greatly minimize ion conduction through the tube. The actuator may be, for example, a solenoid operated piston 121. Such a device is capable of operating at a rate of at least 10 s of Hertz. By timing the actuator operation to the AC cycle, effective DC stimulation can be provided to a desired structure, for example located along path 118, while passing the opposite polarity along path 117.

Although the above implementations describes the ion switch changing state between the two phases of the biphasic pulse, in certain embodiments it may be that it is preferable to pass a number of phase 1s in one direction, from the same or different electrodes, and then reverse the current direction and pass the phase 2 currents later. The same principle applies so that the ion switch would be open during all the phase 1s (or 2s) and closed during all the phase 2s (or 1s). This may be necessary to do if the ion switch speed is too slow to switch between the two phases of a biphasic pulse.

It is noted that firing the nerve using predominantly DC current may produce different perceptual effects for the user. It is possible that new types of simulation strategy may be made available to recipients with different perceptual characteristics. It may be for example that a small amount of DC that is allowed to "bleed" from all the electrodes across all nerves is useful in keeping all the nerves partially depolarized. In a hearing implant, for example, this may in turn induce a background firing rate in the nerves similar to that observed in normal hearing subjects. The lack of background nerve firing in recipients of cochlear implants has been proposed as one reason why cochlear implant recipients perform poorly in noisy listening environments.

Additionally, while embodiments of the present invention have been described with reference to devices that attempt to pass a purely monophasic signal over the auditory nerve (i.e. to maximize the ratio of DC to AC signal), embodiments may be useful to stimulate the nerve with some lesser ratio of DC to AC than the maximum possible. For example, stimulation with a purely monophasic signal may be more power efficient, but perceptually worse than the equivalent biphasic signal. There may for example be some optimum ratio of DC to AC which provides lower stimulation thresholds without perceptual degradation. It will be appreciated that the system described here can easily be modified to pass a combination of monophasic and biphasic signals across the nerve (i.e. to reduce the ratio of DC to AC signal). This could be achieved by adjusting the control signals for the ion switch so that its "off" impedance is less than the maximum value available, allow increased flow of current through it in phase 2 when it is nominally high impedance.

Whilst the discussion has been predominantly in relation to cochlear implants, it will be appreciated that the principle of the present invention is applicable to neural stimulation devices in general.

Although the above described embodiments were discussed with reference to a cochlear implant, in other embodiments these methods and systems may be used with other implant systems such as, for example, in an auditory brain stimulator or other tissue-stimulating prosthesis.

The invention described and claimed herein is not to be limited in scope by the specific preferred embodiments herein disclosed, since these embodiments are intended as illustrations, and not limitations, of several aspects of the invention. Any equivalent embodiments are intended to be within the scope of this invention. Indeed, various modifications of the invention in addition to those shown and described herein will become apparent to those skilled in the art from the foregoing description. Such modifications are also intended to fall within the scope of the appended claims. All documents, patents, journal articles and other materials cited in the present application are hereby incorporated by reference.

The invention claimed is:

1. An implantable tissue stimulating prosthesis for electrically stimulate a segment of a recipient's tissue with a biphasic stimulating current signal, the prosthesis comprising:
   a stimulating contact adapted to be positioned adjacent the tissue segment;
   a reference electrode adapted to be positioned separate from the stimulating contact; and
   a variable bypass pathway adapted to positioned between the stimulating contact and the reference electrode, wherein the pathway has an impedance to a first polarity of the current signal that is greater than the impedance of the tissue segment, and an impedance to a second polarity of the current signal that is less than the impedance of the tissue segment.

2. The prosthesis of claim 1, wherein the variable bypass pathway includes one or more ion switches configured to vary the impedance of the pathway.

3. The prosthesis of claim 2, wherein the one or more ion switches vary the impedance of the pathway in response to control signals received from a stimulator unit.

4. The prosthesis of claim 1, wherein the variable bypass pathway includes one or more ion permeable membranes that allow the flow of ions in only one direction.

5. The prosthesis of claim 1, wherein the stimulating contact is a stimulating electrode.

6. The prosthesis of claim 1, wherein the stimulating contact is an ion switch.

7. The prosthesis of claim 1, wherein the variable bypass pathway comprises a tube having an impedance control contact disposed therein.

8. The prosthesis of claim 7, wherein the impedance control contact comprises one or more of an ion permeable membrane and an ion switch.

9. The prosthesis of claim 7, wherein the ends of the tube are closed to prevent ingrowth of tissue.

10. The prosthesis of claim 7, wherein at least one end of the tube is closed with a solid rod of porous material.

11. The prosthesis of claim 1, wherein the variable bypass pathway comprises a conductive wick.

12. The prosthesis of claim 1, wherein the reference electrode is contained within an enclosure, and a set of ion switches are provided to control conduction across the enclosure.

13. The prosthesis of claim 1, wherein the variable bypass pathway includes one or mechanical valves that vary the impedance of the pathway.

14. A method of electrically stimulating a segment of a recipient's tissue with a tissue stimulating prosthesis comprising a stimulating contact adapted to be positioned adjacent the tissue segment, a reference electrode adapted to be positioned separate from the stimulating contact, and a variable bypass pathway disposed between the stimulating contact and reference electrode, the method comprising:
    delivering a balanced current signal to the tissue segment, wherein a first polarity of the current signal is conducted from the stimulating contact to the reference electrode substantially though the tissue segment, and wherein a second polarity of the current signal is conducted from the stimulating contact to the reference electrode substantially through the variable bypass pathway so as to substantially bypass the tissue segment.

15. The method of claim 14, wherein the variable bypass pathway has an impedance to the first polarity that is greater than the impedance of the tissue segment, and an impedance to the second polarity that is less than the impedance of the tissue segment.

16. The method claim 14, wherein the variable bypass pathway includes one or more ion switches, and wherein the method further comprises:
    closing the one or more ion switches to reduce the impedance of the pathway so that the second polarity passes through the variable bypass pathway.

17. The method of claim 16, further comprising:
    closing the one or more ion switches in response to control signals received from a stimulator unit.

18. The method of claim 14, further comprising:
    periodically reversing the first and second polarities of the current signal.

19. The method of claim 14, wherein the stimulating contact comprises an electrode, and wherein the method further comprises:
    delivering current signals to the tissue via the electrode.

20. The method of claim 14, wherein the stimulating contact comprises an ion switch, and wherein the method further comprises:
    delivering current signals to the tissue via the ion switch.

* * * * *